United States Patent
Jung et al.

(10) Patent No.: US 7,460,219 B2
(45) Date of Patent: Dec. 2, 2008

(54) METHOD FOR OPTICALLY INSPECTING A WAFER BY SEQUENTIALLY ILLUMINATING WITH BRIGHT AND DARK FIELD LIGHT BEAMS WHEREIN THE IMAGES FROM THE BRIGHT AND DARK FIELD ILLUMINATED REGIONS ARE SPATIALLY OFFSET

(75) Inventors: Paul-Gottfried Jung, Florstadt (DE); Albert Kreh, Solms (DE); Henning Backhauss, Wetzlar (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 455 days.

(21) Appl. No.: 11/044,370

(22) Filed: Jan. 27, 2005

(65) Prior Publication Data

US 2005/0168729 A1    Aug. 4, 2005

(30) Foreign Application Priority Data

Jan. 30, 2004    (DE) ................... 10 2004 004 761

(51) Int. Cl.
*G01N 21/00*    (2006.01)
(52) U.S. Cl. .................................. 356/237.2
(58) Field of Classification Search ... 356/237.2–237.5, 356/239.7–239.8
See application file for complete search history.

(56) References Cited

U.S. PATENT DOCUMENTS 5,291,239 A * 3/1994 Jackson ................. 355/53
6,222,624 B1 * 4/2001 Yonezawa .............. 356/237.1
6,633,375 B1 * 10/2003 Veith et al. .............. 356/237.4
2002/0089664 A1 * 7/2002 Shibata et al. ........... 356/237.2
2003/0179369 A1 * 9/2003 Feldman et al. .......... 356/237.2
2003/0227618 A1 * 12/2003 Some ...................... 356/237.1
2005/0259245 A1 * 11/2005 Cemic et al. ............. 356/237.2

* cited by examiner

*Primary Examiner*—Tarifur Chowdhury
*Assistant Examiner*—Tara S Pajoohi
(74) *Attorney, Agent, or Firm*—Houston Eliseeva LLP (57) ABSTRACT

The invention concerns a method for inspecting the surface of a wafer, having at least a first and a second incident illumination device in order to emit respectively a first and a second incident illuminating light beam and to illuminate a region on the surface, and having at least one image sensing device in order to sense an image of the illuminated region, the first incident illumination device and the at least one image sensing device being arranged so that images of the illuminated region can be sensed in a bright-field configuration, and the second incident illumination device and the at least one image sensing device being arranged so that images of the illuminated region can be sensed in a dark-field configuration. A control device for controlling the first and the second incident illumination device and the at least one image sensing device is furthermore provided. The images in the bright-field configuration and the images in the dark-field configuration are acquired with a time offset from one another or with a separation from one another by color.

17 Claims, 6 Drawing Sheets

METHOD FOR OPTICALLY INSPECTING A WAFER BY SEQUENTIALLY ILLUMINATING WITH BRIGHT AND DARK FIELD LIGHT BEAMS WHEREIN THE IMAGES FROM THE BRIGHT AND DARK FIELD ILLUMINATED REGIONS ARE SPATIALLY OFFSET

CROSS-REFERENCE TO RELATED APPLICATIONS

This application claims priority of the German patent application 10 2004 004 761.8 which is incorporated by reference herein.

FIELD OF THE INVENTION

The present invention concerns a method for inspecting a wafer.

BACKGROUND OF THE INVENTION

In semiconductor production, wafers are sequentially processed in a plurality of process steps during the production process. With increasing integration density, demands in terms of the quality of the features configured on the wafers are rising. It is advantageous, for this purpose, if the quality of even individual process steps, for example lithography steps, can be reliably assessed during the manufacturing process and before any subsequent process step. Thus, if a determination is made, just after a process step is performed and even before a production process has been completed, that a wafer or features configured on the wafer are defective, the wafer can be immediately discarded with no need to perform additional subsequent process steps. Or the wafers found to be defective can be reprocessed separately until satisfactory quality is achieved. Efficiency and yield in semiconductor production can thereby be enhanced.

Optical apparatuses are particularly suitable for inspecting the surface of wafers. Optical apparatuses are known that, by image recognition, can recognize a wide variety of features on the surface of a wafer. Wafer inspection apparatuses of this kind operate either in a bright-field configuration, in which the surface of the wafer is illuminated and the light reflected from the surface is sensed by a camera, or in a dark-field configuration, in which the surface of the wafer is illuminated and the light scattered from defects, particles and the like is sensed by a camera. In a wafer inspection apparatus of this kind, the surface of the wafer can also be illuminated stroboscopically, i.e. with short flashes of light.

Images acquired in a bright-field and a dark-field configuration are informative in different ways. For optimum wafer inspection, it is therefore desirable to sense images with a wafer inspection apparatus in both a bright-field and a dark-field configuration. In order to achieve high accuracy in the detection of defects on the surface of wafers in a dark-field configuration, a high intensity of the light flashes used to illuminate the surface is desirable.

BRIEF SUMMARY OF THE INVENTION

It is the object of the present invention to develop a method for inspecting a wafer to the effect that both bright-field images and dark-field images are acquired with high accuracy, with comparatively little mutual influencing of the bright-field and dark-field images and at the same time with high throughput.

This object is achieved by way of a method for inspecting wafers having at least a first and a second incident illumination device and at least one image sensing device being provided, the first incident illumination device being provided in a bright-field configuration and the second incident illumination device in a dark-field configuration, the method comprises the steps of:

illuminating a region on the surface of a wafer with the first incident illumination device in the bright-field configuration;

illuminating the region on the surface of a wafer with the second incident illumination device in the dark-field configuration; and controlling the first and the second incident illumination device and the at least one image sensing device by means of a control device in such a way that an acquisition of a plurality of images of the illuminated region in the bright-field configuration and an acquisition of a plurality of images of the illuminated region in the dark-field configuration is accomplished with the image sensing device, with a time offset from one another.

According to the present invention, an apparatus for inspecting the surface of a wafer is made available, having at least a first and a second incident illumination device in order to emit respectively a first and a second incident illuminating light beam and to illuminate a region on the surface, and having at least one image sensing device in order to sense an image of the illuminated region, the first incident illumination device and the at least one image sensing device being arranged so that images of the illuminated region can be sensed in a bright-field configuration, and the second incident illumination device and the at least one image sensing device being arranged so that images of the illuminated region can be sensed in a dark-field configuration. According to the present invention, the wafer inspection apparatus is characterized in that a control device for controlling the first and the second incident illumination device and the at least one image sensing device is provided, so that the plurality of images in the bright-field configuration and the plurality of images in the dark-field configuration are acquired with a time offset from one another or are separated by color.

As a result of the separation of the bright-field and dark-field images in time or by color, a mutual influencing of the bright-field and dark-field images is avoided. It is advantageous that according to the present invention, greater signal-to-noise ratios can be achieved in particular for the dark-field images, so that the accuracy with which defects are detected can advantageously be enhanced especially in the dark-field images.

The incident illumination devices used for illumination in the bright-field and the dark-field configuration are preferably operated stroboscopically, i.e. they emit comparatively short illuminating light flashes that are imaged onto the surface of the wafer. In this preferred embodiment, the illuminating light flashes for bright-field images and for dark-field images are therefore also offset in time from one another.

According to a preferred embodiment, at least two incident illumination devices and one image sensing device are provided for sensing both bright-field and dark-field images. Whereas the one incident illumination device is arranged in a bright-field configuration so that light is reflected from the surface of the wafer directly into the associated image sensing device, the other of the two incident illumination devices is arranged in a dark-field configuration so that only scattered light, or light diffracted by the surface of the wafer, is imaged into the associated image sensing device. In this configuration, the incident illumination devices preferably alternatingly emit illuminating light flashes that are employed alternatingly for a bright-field image and a dark-field image.

More incident illumination devices and/or image sensing devices can of course be provided according to the present invention, and they can be selectably operated in order to implement sensing of both bright-field images and dark-field images using the same wafer inspection apparatus. The incident illumination devices and/or the image sensing devices are preferably activated as necessary by means of a central processor unit, for example a computer, as the control device.

An advantageously high throughput for the wafer inspection apparatus can be achieved according to the present invention if a movement device, or a beam deflection device that encompasses an optical element provided in a beam path for appropriate deflection of the incident illuminating light beam, is additionally provided in order to move the wafer and the incident illuminating light beam relative to one another. In this context, the control device activates the movement device or beam deflection device so that the images in the bright-field configuration and the images in the dark-field configuration are acquired with not only a time offset but also a spatial offset from one another.

In this embodiment, the illuminating light flashes sequentially scan the entire surface of the wafer. The relative shift of the wafer and the illuminating light flashes necessary for this is preferably distributed uniformly over the sequence of illuminating light flashes. Although in this embodiment it may be necessary to operate the image sensing device at a higher frequency, this can readily be achieved with suitable provisions, for example frame grabber cards with a high readout frequency, or by the use of two data readout devices for alternatingly reading the sensed images out of the image sensing device.

According to a preferred embodiment, the imaging of the illuminating light flashes is not modified over time, and the wafer is moved relative to the first and the second incident illuminating light beam. The control device thus controls the movement device so that the wafer is moved, at least locally, in continuous or timed fashion relative to the first and the second incident illuminating light beam. For this purpose, the wafer can be rotated in continuous or timed fashion, or the wafer can be received on an X-Y translation stage, activated in continuous or timed fashion, that is driven e.g. by a stepping motor or the like.

According to the present invention, the relative displacement of the wafer and of the illuminating light beams is coordinated with the sequence of illuminating light flashes so that the bright-field images of regions periodically offset from one another on the surface of the wafer are acquired. These regions periodically offset from one another are defined so that the entire surface of the wafer can be sequentially scanned; in particular, the regions offset from one another overlap or are immediately adjacent to one another. The regions periodically offset from one another can correspond to at least one die, to the entire surface of a single die, or to a sub-region of a die. This can easily be ensured by suitable calibration of the wafer inspection apparatus. In that context, the bright-field images can extend a definable number of pixels or image points beyond the edge of the die or beyond the edges of the dice sensed as a whole, thus always ensuring that, even taking into account tolerances of the wafer inspection apparatus, the entire surface of at least one die is sensed with one bright-field image.

According to a further embodiment, the control device controls the first and the second incident illumination device and/or the image sensing device so that between two images that are acquired in the bright-field configuration, at least two images, in very particularly preferred fashion exactly two images, are acquired in the dark-field configuration. The dark-field images can be acquired at different orientations of the respective incident illumination devices with respect to the wafer. For example, the incident illumination device used for a first light flash for a first dark-field image can be aligned so that a projection of the illumination axis defined by the incident illumination device onto the surface of the wafer having the features configured on the wafer encloses a first angle, for example a 45-degree angle; and the incident illumination device used for a second light flash for a second dark-field image can be aligned so that a projection of the illumination axis defined by the incident illumination device onto the surface of the wafer having the features configured on the wafer encloses a second angle that is different from the first angle, for example a 90-degree angle. It is thereby possible in simple fashion to obtain additional information about any defects and/or particles present on the wafer.

In this context, the control device can also activate the first and the second incident illumination device and/or the image sensing device so that the images in the dark-field configuration that are acquired between the bright-field images are acquired simultaneously. An even higher throughput for the wafer inspection apparatus can thus be attained.

Because the images that are acquired in the dark-field configuration preferably contain regions of at least two adjacent dice on the surface of the wafer, it is useful to make provisions so that the location of the respective dice at the moment the respective dark-field images are sensed is known. The location of a respective die can be calculated, in principle, by suitable calibration of the wafer inspection apparatus and by calculating the respective location from the illumination sequence used and from the respective movement sequence of the wafer.

According to a further preferred embodiment, however, the location of the respective die is determined actively at the moment the dark-field images are sensed. For that purpose, the control device can control the first and the second incident illumination device and/or the image sensing device so that an image can be acquired simultaneously with the dark-field configuration and with the bright-field configuration, the image acquired with the bright-field configuration having a lower incident illuminating light beam intensity. Because of the lower intensity of the light flashes used for the further bright-field image, any mutual influencing of the bright-field and dark-field images is thus also further minimized.

According to the present invention, a separation of the bright-field and dark-field images by color can be provided alternatively or in addition to the separation in time. A polychromatic incident illumination device having several color channels is usefully used for this purpose, the control device activating a predetermined one of the several color channels of the respective polychromatic incident illumination device for sensing of the image in the dark-field configuration at the lower incident illuminating light beam intensity. Sensing of the bright-field image is accomplished in the predetermined color channel, during sensing of the dark-field images, in the remaining color channels or all the other color channels of the respective image sensing device used for sensing of the dark-field images. On the basis of the additionally acquired bright-field image, from which features on the surface of the wafer such as "streets" or markings may readily be deduced, it is thus possible to ascertain the current positioning of the wafer at the moment the dark-field images are sensed.

If the color channel used for the bright-field image with the low intensity is, for example, the red color channel (R) or the blue color channel (B) of the associated incident illumination device, sensing of the dark-field images is then performed in the remaining color channels of the image sensing device, for example in the green (G) and blue (B) color channels or in the red (R) and green (G) color channels of a color-sensitive image sensing device having R, G, and B color channels. This additional separation by color is not absolutely necessary, however; sensing of the dark-field images can instead also be accomplished in all the color channels of the image sensing device.

In this embodiment an image evaluation device, for example a pattern recognition software program, is preferably provided in order to identify, on the basis of the bright-field image acquired in the bright-field configuration at the lower incident illuminating light beam intensity, features and/or individual dice on the surface of the wafer, for example "streets" or markings on the surface of the wafer. With a knowledge of the location of the die, it is then possible to draw conclusions, from the image information of the dark-field images, as to the exact location of defects and/or particles on the surface of the wafer at the moment the respective dark-field images are acquired.

According to another aspect, the present invention also concerns a method for inspecting a wafer. The method is designed to operate the apparatus described in this Application, and can be stored in the form of a control program or software program on a computer-readable or machine-readable medium, for example on a magnetic or optical data medium or a semiconductor memory element, in order to be retrieved and executed by a computer or processor acting as the control device.

BRIEF DESCRIPTION OF THE DRAWINGS

The invention will be described below in exemplifying fashion and with reference to the attached drawings, from which further features, advantages, and objects to be achieved are evident. In the drawings.

In the Figures, identical reference characters refer to identical or substantially identically functioning elements or groups of elements.

DETAILED DESCRIPTION OF THE INVENTION

A wafer inspection apparatus in accordance with the present invention will be described below with reference to FIGS. 5 and 6. FIG. 6 is a schematic side view showing a wafer inspection apparatus in accordance with the present invention. According to FIG. 6, the wafer inspection apparatus labeled with the overall reference character 1 encompasses two incident illumination devices 2, 2' that emit a respective incident illuminating light beam 37 in order to illuminate a region 8 on surface 32 of wafer 6. According to FIG. 6, wafer inspection apparatus 1 furthermore encompasses a camera, functioning as an image sensing device, in order to sense an image of illuminated region 8 on surface 32 of wafer 6. Camera 4 can be a matrix camera or linear camera that senses monochromatic or color images, preferably having R, G, and B color components. In FIG. 6, reference character 30 schematically designates all the color channels of camera 4 that are suitable for reading out color image data, for example in the primary colors RGB. According to FIG. 6, imaging axis 10 defined by camera 4 extends perpendicular to surface 32 of wafer 6. Objective 5 placed in front of camera 4 images illuminated region 8 onto the image plane of camera 4. The image data sensed by camera 4 are read out via a data line 13 by computer 14 acting as data readout device, and are temporarily stored or further processed there. Lastly, the image data are displayed on a monitor or display 15. Preferably only one camera 4 is provided according to the present invention, but in principle several cameras 4 can also be provided.

According to FIG. 6, incident illumination device 2 has associated with it a light source 11 whose light is fed via a light guide or light-guiding bundle 12 into incident illumination device 2, for example a glass-fiber illuminated field or a glass fiber linear array. An objective or lens 3 images incident illuminating light beam 37 onto surface 32 of wafer 6, but need not necessarily be provided. According to FIG. 6, incident illumination device 2 defines an illumination axis 9 that is inclined at an angle $\alpha$ relative to the lines normal to surface 32 of the wafer and relative to imaging axis 10.

According to FIG. 6, incident illumination device 2' has associated with it a light source 11' whose light is coupled via a light guide or light-guiding bundle 12' into incident illumination device 2'. The light beam emitted from incident illumination device 2' is reflected from the front side of beam splitter mirror 50 onto surface 32 of wafer 6, so that the illumination axis of incident illumination device 2' coincides with imaging axis 10 of camera 4.

According to FIG. 6, incident illumination device 2' is arranged in a bright-field configuration, so that the light reflected from illuminated region 8 on surface 32 of wafer 6 passes through beam splitter mirror 50 and is imaged into camera 4. According to FIG. 6, incident illumination device 2 is arranged in a dark-field configuration, so that illuminating light beam 37 is not reflected from surface 32 of wafer 6 directly into camera 4. Instead, all that is imaged into camera 4 of incident illuminating light beam 37 is scattered light that derives, for example, from defects or particles in illuminated region 8, or diffracted light.

According to FIG. 6, wafer 6 is held on a wafer receiving device 7, for example on a vacuum clamping apparatus (vacuum chuck) or an electrostatic clamping apparatus (electrostatic chuck). Wafer 6 is held movably on wafer receiving device 7, so that wafer 6 can be moved in continuous or timed fashion relative to the incident illuminating light beams, for example by rotation of wafer 6 about the line normal to surface 32 of wafer 6 passing through incidence point 35, or by translational displacement of wafer 6 in two mutually orthogonal spatial directions in the plane of wafer 6.

Figure 5:
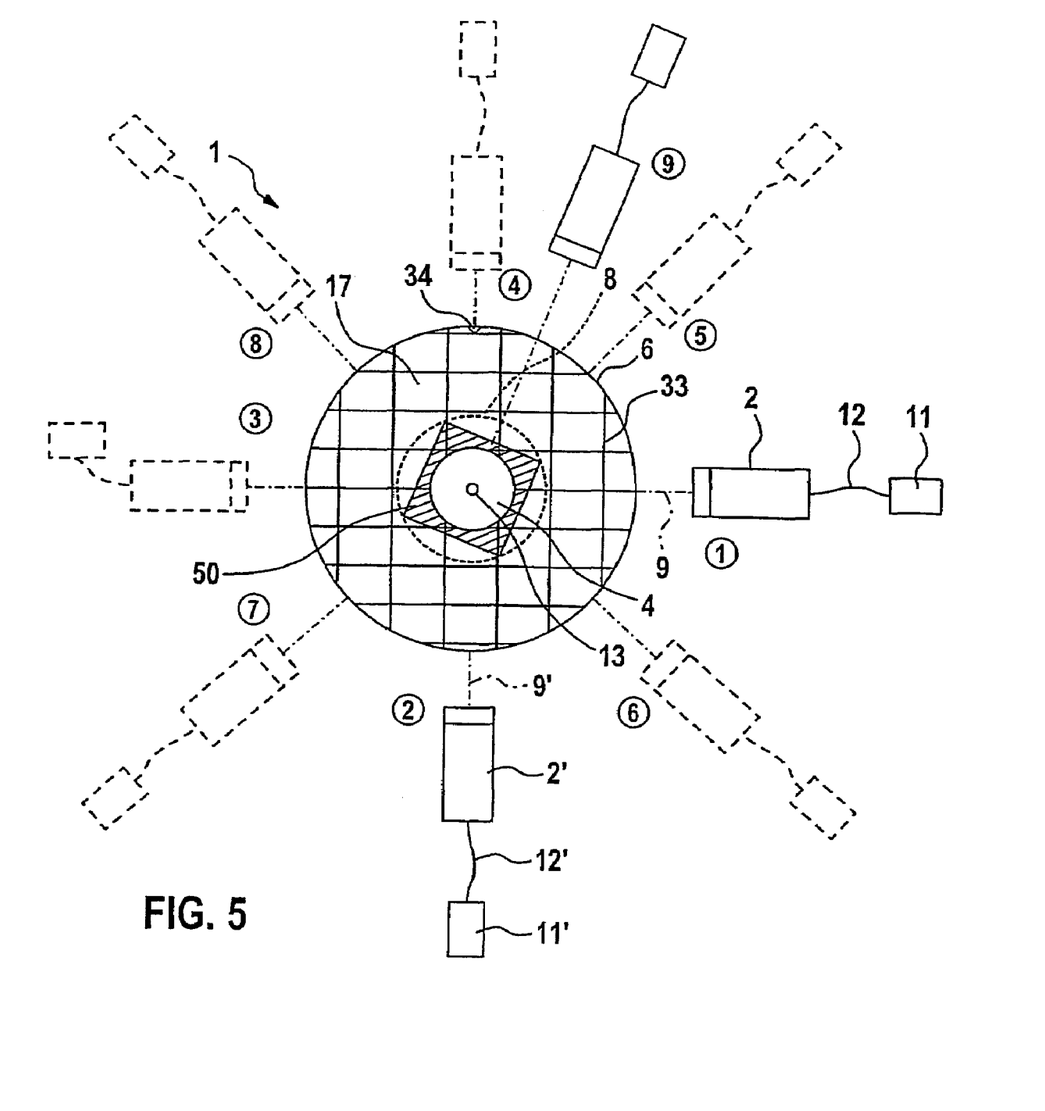
FIG. 5 is a schematic plan view showing a wafer inspection apparatus in accordance with FIGS. 2 through 4.
Figure 6:
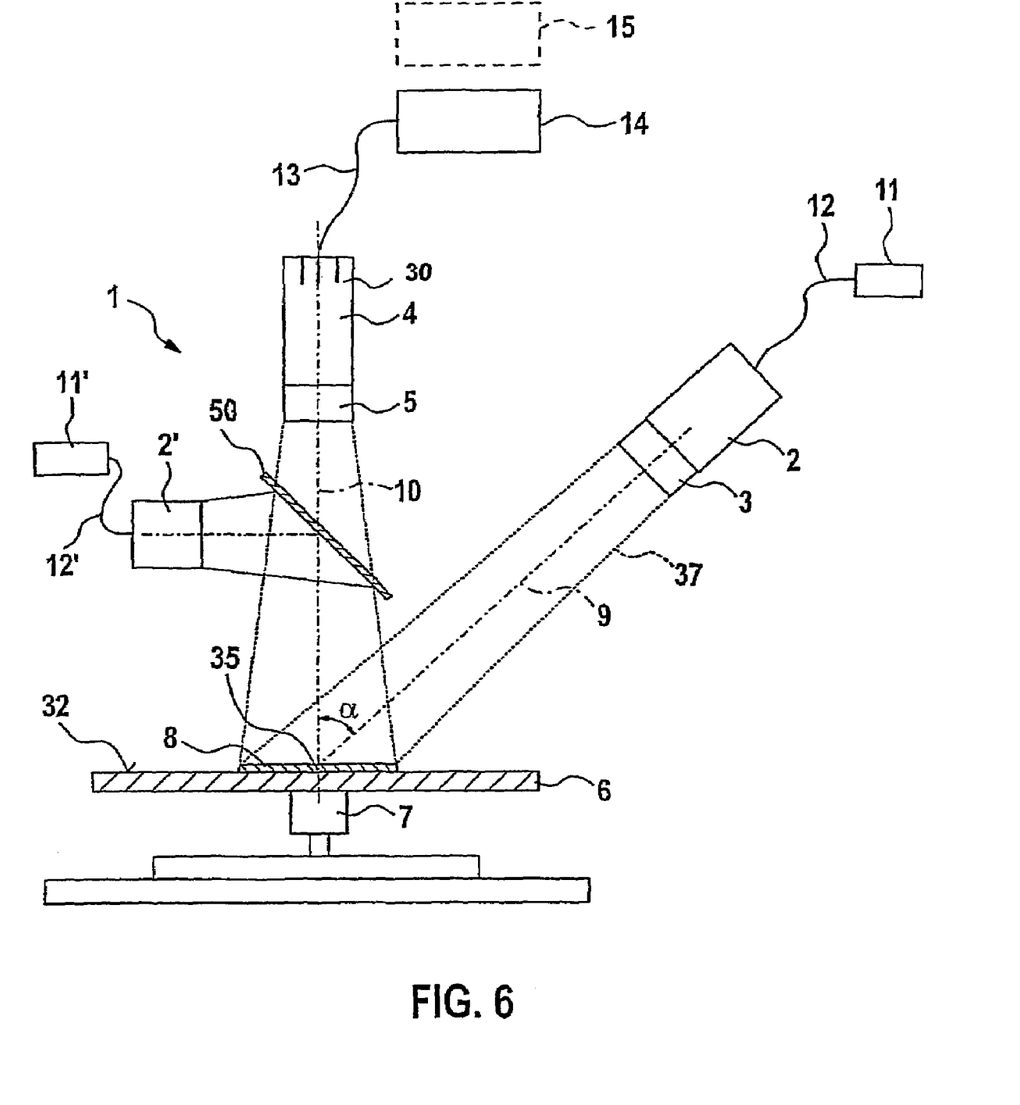
FIG. 6 is a schematic side view showing a wafer inspection apparatus according to a further embodiment in accordance with the present invention.

FIG. 5 is a plan view of the wafer inspection apparatus according to FIG. 6. According to FIG. 5, the two incident illumination devices 2, 2' are arranged at right angles to one another at two positions labeled with the circled numbers 1 and 2. According to FIG. 5, wafer 6 is held on wafer receiving device 7 in a predefined orientation. A notch 34, a flat (not depicted), or a marking on the surface of wafer 6 serves for alignment of wafer 6. A wafer aligner can be provided for alignment of wafer 6, or wafer 6 that is already aligned in a defined fashion can be transferred, by means of a gripper arm or the like, to the wafer receiving device in a predefined alignment.

As shown in FIG. 5, a plurality of dice 17 are configured on wafer 6, and linear features 33 such as so-called "streets," which preferably intersect one another at right angles, are configured on the surface of wafer 6. According to FIG. 5, the projections of illumination axes 9, 9' onto the surface of wafer 6 extend parallel or at right angles to linear features 33 on the surface of wafer 6.

As indicated in FIG. 5 by the dashed lines, further incident illumination devices can be arranged along the periphery of wafer 6, specifically at angular spacings relative to incident illumination device 2 (labeled with the number 1) that correspond to an integral multiple of 45° or 90°. These possible positions are labeled in FIG. 5 with the circled numbers 3 through 8. These further incident illumination devices are, of course, not absolutely necessary, but if they are present they can optionally be activated selectably by means of a central control device.

According to FIG. 5, camera 4 is arranged on the central perpendicular onto the surface of wafer 6, in order to detect light scattered from the surface of wafer 6 that derives from illumination by one of the incident illumination devices labeled with the numbers 1 through 8.

According to FIG. 5, a further incident illumination device is arranged at the position labeled with the number 9, and emits a light beam substantially parallel to the surface of wafer 6. As shown in FIG. 6, this light beam is reflected by the front side of beam splitter mirror 50 perpendicularly onto the surface of wafer 6. Whereas, according to FIG. 5, incident illumination devices 2 provided at the positions labeled with the numbers 1 through 8 are arranged in a dark-field configuration, incident illumination device 2 provided at the position labeled with the number 9 is arranged in a bright-field configuration.

For operation of the wafer inspection apparatus, the incident illumination devices are operated stroboscopically in order to emit short light flashes, for example having a flash duration of approximately 15 microseconds, onto the surface of wafer 6. The exact sequence of illuminating light flashes will be described in more detail below with reference to FIGS. 1 through 4. Between the light flashes the wafer is shifted continuously, or according to an alternative embodiment also in timed fashion and synchronously with image sensing, so that images of regions periodically offset from one another on the wafer surface are sensed and ultimately the entire wafer surface is scanned sequentially. A new exposure cycle then starts. The images of illuminated region 8 on surface 32 of wafer 6 sensed by camera 4 are read out in synchronization with the illuminating light flashes, for example by a frame grabber card, and conveyed to a computer, where these image data are temporarily stored or further processed, for example for graphical image evaluation and image display on monitor 15.

Figure 1:
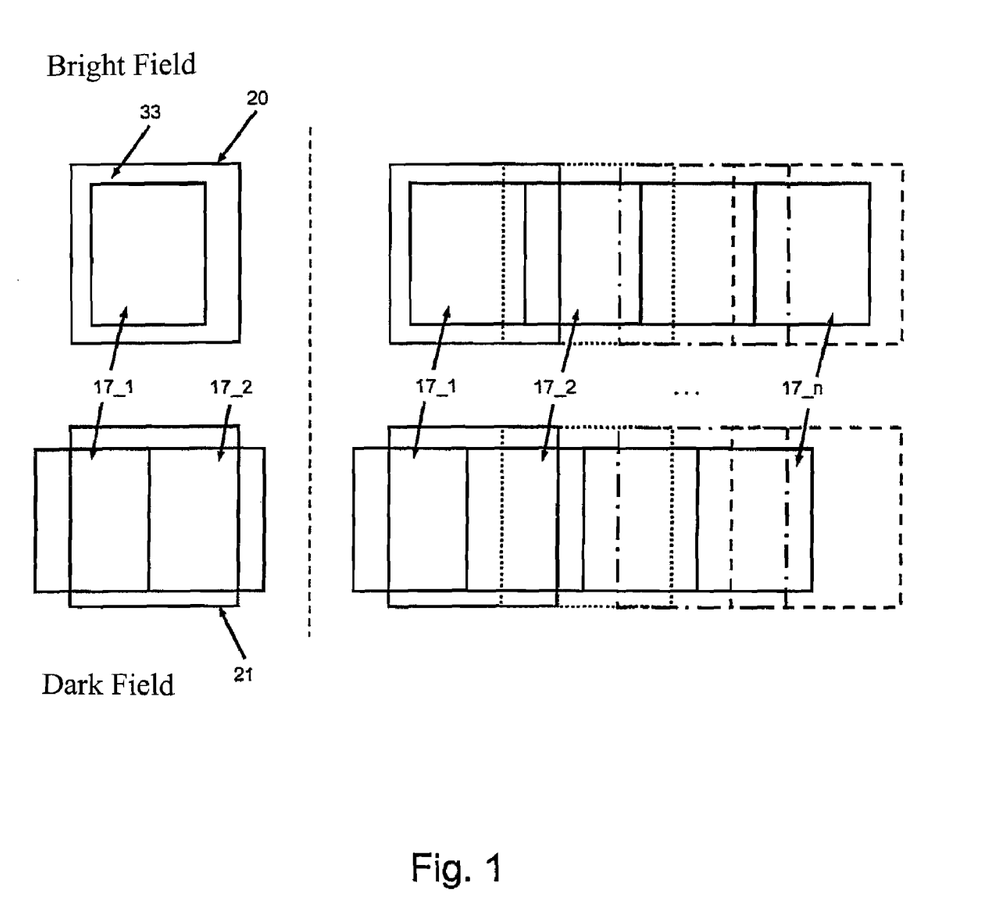
FIG. 1 is a schematic plan view of a wafer showing a sequence of image regions that are sensed by a wafer inspection apparatus in accordance with the present invention.

FIG. 1 shows, in a schematic plan view of a wafer, a sequence of images that are sensed with the wafer inspection apparatus in accordance with the present invention shown in FIGS. 5 and 6. In the left portion of FIG. 1, the sequence is depicted by way of example for an individual die 17_1 singled out by way of example; in the right portion of FIG. 1, the sequence is depicted for a substantially rectangular succession of adjacent dies 17_1, 17_2, ... 17_n on the surface of the wafer. According to FIG. 1, the individual dice are delimited by linear features 33, for example "streets," on the surface of the wafer.

According to the left portion of FIG. 1, in the context of an image sensed in a bright-field configuration, for example acquired by means of camera 4 arranged above wafer 6 and the incident illumination device labeled with the number 9 in FIG. 5, image field 20 encompasses a single die 17_1. To ensure that an image of the entire die 17_1 can reliably be sensed, image field 20 is a few pixels larger than the region of die 17_1. Centering of die 17_1 in image field 20 can be achieved by suitable calibration of the wafer inspection apparatus.

According to FIG. 1, the incident illumination device used for image sensing in the bright-field configuration is operated stroboscopically, and the wafer is shifted one die further between two illuminating light flashes.

Image field 21 for a corresponding image acquisition in a dark-field configuration is depicted in the lower part of FIG. 1. The bright-field and dark-field acquired images are depicted separately in FIG. 1 for reasons of clarity. As may be inferred from the lower part of FIG. 1, at the moment a dark-field image is sensed, wafer is shifted one-half die width relative to the bright-field configuration depicted in the upper part of FIG. 1. In the dark-field configuration, the camera thus senses regions of two adjacent dies 17_1 and 17_2, 17_3 and 17_4, ..., as depicted in FIG. 1 by the image regions shown with different dash patterns.

As is evident from FIGS. 5 and 6, the same camera is used for the images acquired in the bright-field configuration and the images acquired in the dark-field configuration, for example the camera arranged perpendicularly above the wafer as shown in FIG. 5. The incident illumination device at the position labeled with the number 9 in FIG. 5 is used for the images acquired in the bright-field configuration. Any of the incident illumination devices labeled with the numbers 1 through 8 in FIG. 5 can be used for the images acquired in the dark-field configuration in accordance with the lower part of FIG. 1.

As is evident from FIG. 1, the bright-field and dark-field images are acquired separately by means of asynchronously timed flashes, so that the bright-field and dark-field acquired images do not influence one another. According to the present invention, a high throughput for the wafer inspection apparatus can be achieved by the fact that the wafer is moved continuously, so that the bright-field and dark-field images are also automatically acquired in spatially separate fashion.

Figure 2:
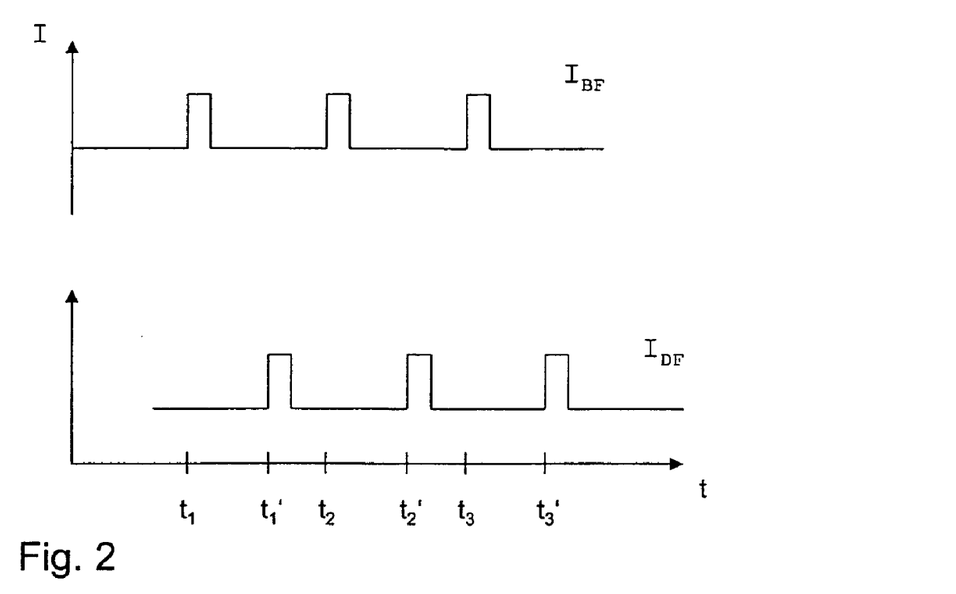
FIG. 2 is a timing diagram for controlling illuminating light flashes of a wafer inspection apparatus of a first embodiment in accordance with the present invention.

FIG. 2 shows a timing diagram for controlling illuminating light flashes for the sequence of images according to FIG. 1. The illuminating light flashes for sensing an image in a bright-field (BF) configuration are depicted in the upper part of FIG. 2, whereas the light flashes used for acquiring an image in the dark-field (DF) configuration are depicted in the lower part of FIG. 2. The illuminating light flashes for acquiring an image in the bright-field configuration are emitted at times t1, t2, t3, etc., while the illuminating light flashes for sensing an image in the dark-field configuration are emitted at times t1', t2', t3', etc. As is evident from FIG. 2, the intensity of the light flashes used for sensing an image in a bright-field configuration has already decayed when the light flashes used for sensing an image in the dark-field configuration are emitted. The images acquired in the dark-field configuration are thus not influenced by the light flashes used for images acquired in a bright-field configuration, and conversely the images acquired in the bright-field configuration are not influenced by the light flashes used for acquiring an image in a dark-field configuration. The signal-to-noise ratio of the sensed images, in particular the dark-field images, can thereby be improved.

An advantageously high throughput for the wafer inspection apparatus is obtained if the wafer is moved continuously. The light flashes that are used for sensing an image in the bright-field configuration preferably are synchronized in accordance with the movement speed of the wafer so that as shown in FIG. 1, in the bright-field configuration image regions 20 contain a complete die. According to FIG. 2, the light flashes used for image acquisition in the dark-field configuration are synchronized so that as shown in FIG. 1, in the dark-field configuration image fields 21 contain portions of two adjacent dice. With a knowledge of the movement speed of the wafer and the synchronization of the light flashes used for image sensing in the dark-field configuration, the location of the boundary line between the two adjacent dice sensed in the dark-field configuration can be calculated.

The illuminated region on the surface of the wafer can, of course, also encompass several dice or a sub-region of one die.

In accordance with the present invention, several images can also be sensed in a dark-field configuration between two light flashes used for sensing an image in the bright-field configuration. This is described by way of example with reference to FIG. 3.

Figure 3:
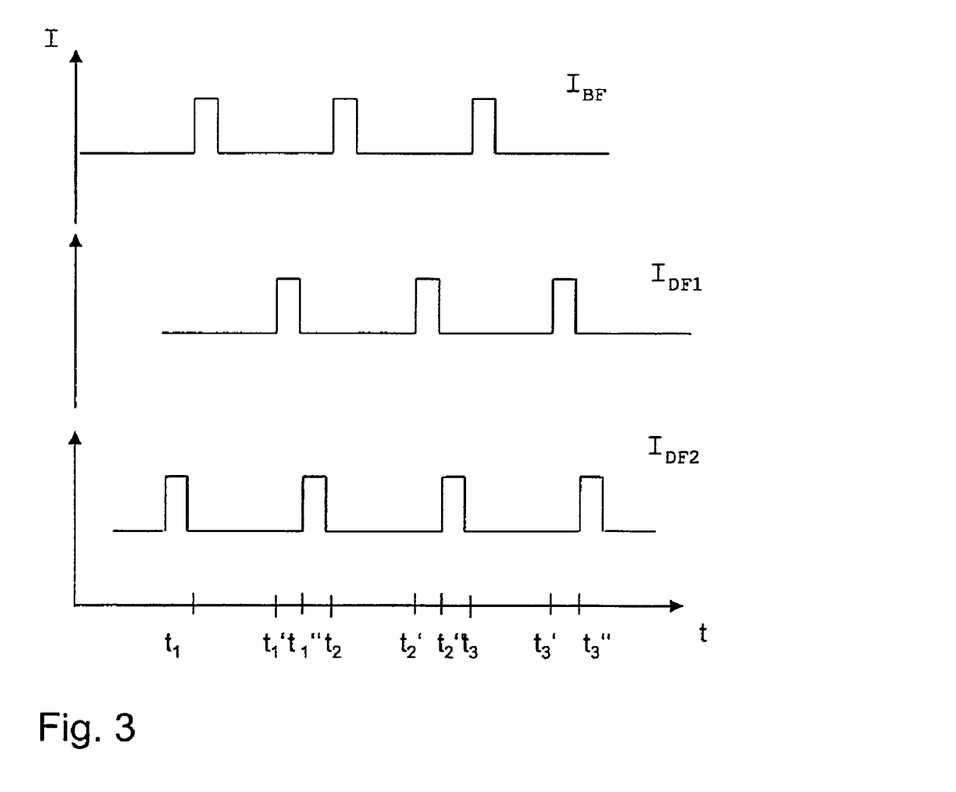
FIG. 3 is a timing diagram for controlling illuminating light flashes of a wafer inspection apparatus of a second embodiment in accordance with the present invention.

According to FIG. 3, two light flashes for acquiring images in a respective dark-field configuration DF1 and DF2 are emitted between two light flashes BF used for acquiring an image in a bright-field configuration. Between the individual image acquisitions, the wafer is moved further in the manner described above, so that different portions of two adjacent dice are sensed in each of the dark-field configurations DF1 and DF2.

In the context of an image acquisition according to the aforesaid FIGS. 2 and 3, care must always be taken that the image regions sensed in the dark-field configuration, which are labeled in the lower part of FIG. 1 with the reference character 21, overlap one another or at least are directly adjacent to one another, so that the entire surface of the wafer can ultimately be scanned by means of the sequence of acquired images to allow defects or particles to be sensed on the entire surface of the wafer.

It is sufficient in principle, for a determination of the position of the individual dice at the moment of an image acquisition in a dark-field configuration, if the wafer inspection apparatus is calibrated and the movement sequence of the wafer is known. From this information, the position of a die at the moment an image is acquired in a respective dark-field configuration can easily be calculated. The present invention is not limited, however, to calculating of the positions of the dice in the dark-field configuration. The respective position of a die can also be actively determined in the context of an image acquisition in a dark-field configuration, as will be described in more detail below with reference to FIG. 4.

Figure 4:
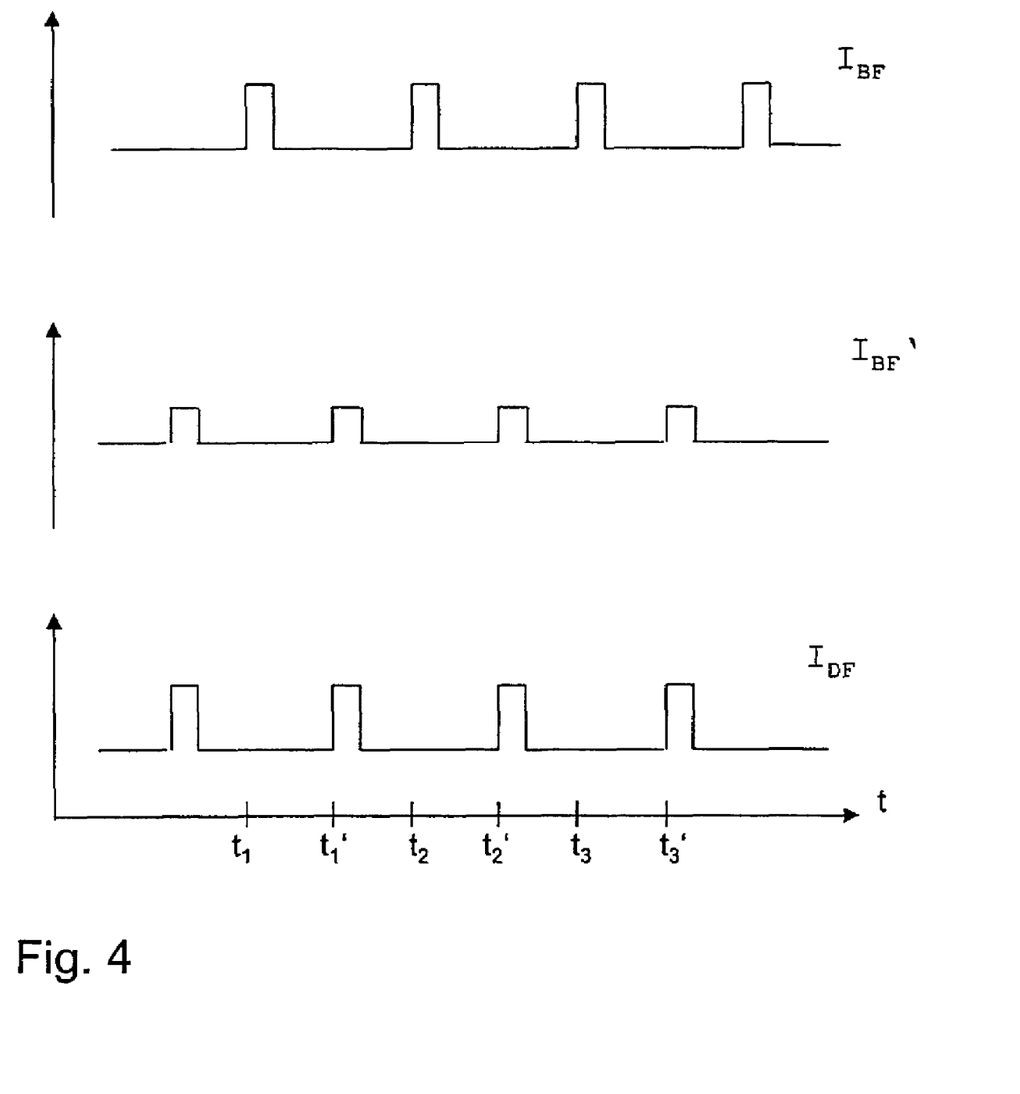
FIG. 4 is a timing diagram for controlling illuminating light flashes of a wafer inspection apparatus of a third embodiment in accordance with the present invention.

FIG. 4 is based on the assumption of the sequence of illuminating light flashes according to FIG. 2, i.e. illuminating light flashes in a bright-field configuration (IBF) and illuminating light flashes in a dark-field configuration (IDF). "Streets," or the linear features labeled with the reference character 33 in FIG. 5, or other suitable markings on the surface of the wafer, are particularly suitable for determining the location of individual dice on the surface of the wafer. It is known that such features are, at best, difficult to resolve in a dark-field configuration.

A procedure in accordance with the present invention for resolving such features is described below with reference to FIG. 4. According to FIG. 4, simultaneously with the illuminating light flashes (IDF) used for sensing an image in the dark-field configuration, a further illuminating light flash is emitted in a bright-field configuration (IBF'), preferably with less intensity. One shared camera senses both the images in the bright-field configuration and the image in the dark-field configuration. To prevent mutual influencing of the images in the bright-field and dark-field configurations, a separation by color of the bright-field and dark-field acquired images is additionally performed, as follows:

Let it be assumed below, by way of example, that the light sources of the incident illumination devices used for bright-field illumination and for dark-field illumination are polychromatic, having several color channels (not depicted) for controlling the spectrum emitted by the respective incident illumination device. For bright-field illumination, however, only one color channel of the relevant incident illumination device is activated, so that a colored light flash, for example a red light flash, is emitted as illumination for the further bright-field image acquisition. Whereas the red channel of the camera is read out for the bright-field image acquisition, for the dark-field image acquisition the remaining color channels are read out, i.e. for example the green (G) and blue (B) color channels of an RGB camera, or all the color channels (reference character 30 in FIG. 6) of the RGB camera are read out. A separation by color of the bright-field and dark-field acquired images is brought about in this fashion. Alternatively, monochromatic light flashes of different colors can be used for the bright-field illumination and the dark-field illumination. Let it be assumed by way of example that a blue light flash is used for the bright-field illumination, and a polychromatic light flash, or one having a color other than blue, is used for the dark-field illumination. The blue color channel of the RGB camera is then read out for the bright-field image acquisition, and the remaining channels of the RGB camera, i.e. the green and red color channels, are read out for the dark-field image acquisition, or all the color channels of the RGB camera are read out for the dark-field image acquisition.

As will be readily apparent to one skilled in the art, monochromatic illuminating light flashes having different colors for an image acquisition in a bright-field configuration and an image acquisition in a dark-field configuration can also be used for separation by color.

From the further image acquired in the bright-field configuration, conclusions can be drawn as to the location of the edges of an individual die. An image evaluation system with suitable pattern recognition, as is well known in the existing art, is used for this purpose. On the basis of these edges, the pixels of the image acquired in the dark-field configuration can be unequivocally allocated to the two adjacent dice, and a conclusion can be drawn as to the location of defects on the surface of the wafer.

According to a further embodiment of the present invention, the acquired images sensed in the bright-field configuration and in the dark-field configuration are separated by color. In accordance with this procedure, the incident illumination devices used for the bright-field configuration and for the dark-field configuration can emit polychromatic light flashes. In accordance with this procedure, however, the incident illumination devices are activated so that the light flashes used for an image acquisition in a bright-field configuration and for an image acquisition in a dark-field configuration exhibit different color spectra that substantially do not overlap one another. For example, the light flash used for image acquisition in the bright-field configuration can be emitted in the red (R) spectral region, and the light flash used for image acquisition in the dark-field configuration can be emitted in the green (G) and/or blue (B) spectral region, in which case the image data of the camera are read out so that the red image data are read out for a bright-field acquired image and the green and/or blue image data for a dark-field acquired image. A separation by color is brought about in this fashion. With this embodiment the images in the bright-field and dark-field configurations can be acquired simultaneously, and can depict identical surface regions of the wafer.

Figure 7:
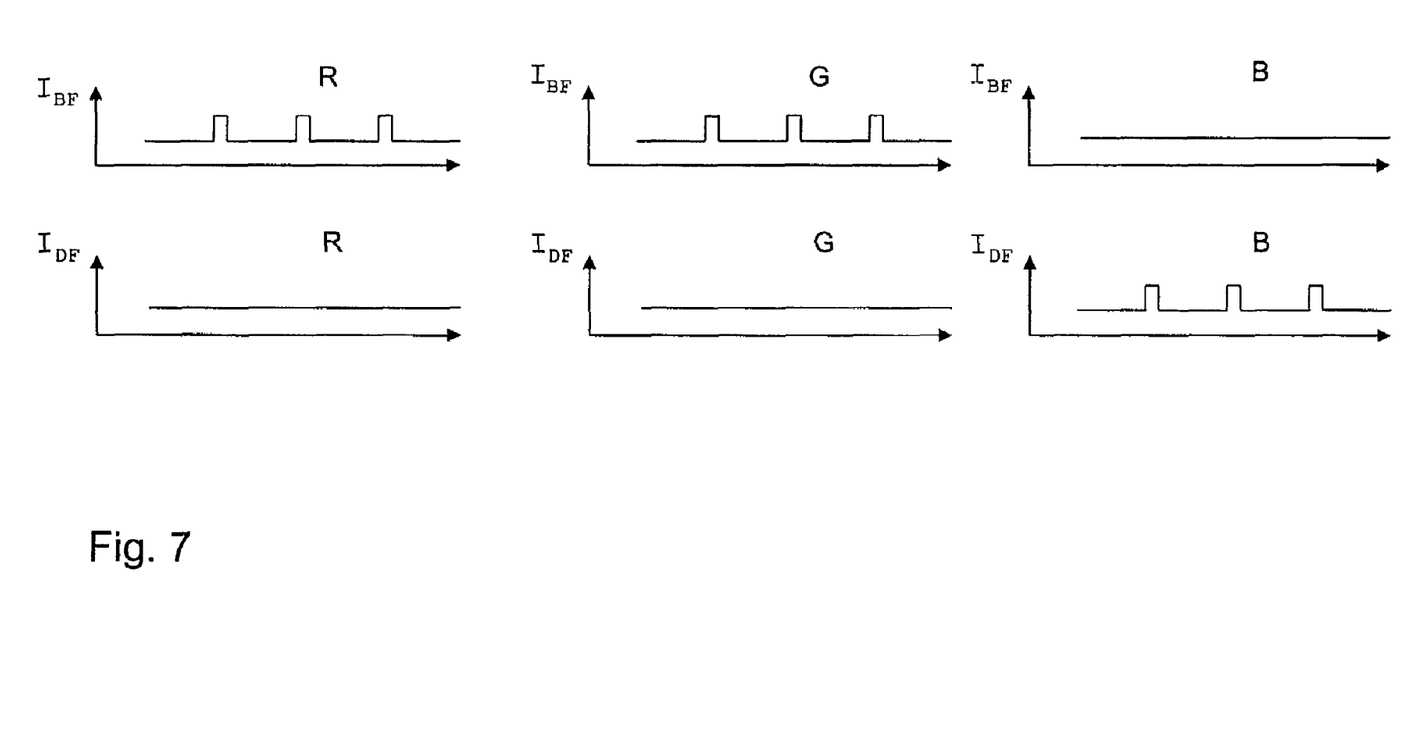
FIG. 7 is a timing diagram for controlling illuminating light flashes of a wafer inspection apparatus of a fourth embodiment in accordance with the present invention.

This procedure is summarized schematically in FIG. 7, which depicts a timing diagram for controlling illuminating light flashes of a wafer inspection apparatus of a fourth embodiment in accordance with the present invention. The upper part of FIG. 7 depicts the light flashes used for illumination in the bright-field (BF) configuration, separated into R (red), G (green), and B (blue) spectral components. The lower part of FIG. 7 correspondingly depicts the light flashes used for illumination in the dark-field (DF) configuration. Whereas light flashes having red and green spectral components are used for illumination in the bright-field configuration, light flashes having exclusively a blue spectral component are used for illumination in the dark-field configuration. These light flashes are emitted synchronously and isochronously.

According to FIG. 7, the red and green color channels of the camera are read out for image sensing in the bright-field configuration. According to FIG. 7 only the blue color channel of the camera is read out for image sensing in the dark-field configuration.

According to a further embodiment, the incident illumination devices used for bright-field image acquisition and those for dark-field image acquisition are monochromatic colored light sources, light flashes having different spectral components being used for image acquisition in the bright-field and in the dark-field configuration. For example, the images acquired in the bright-field configuration can be acquired with red illuminating light flashes, and the images acquired in the dark-field configuration can be acquired with green and/or blue illuminating light flashes. For separation by color, the color channels of the camera can then be read out separately and allocated to the acquired images in the manner described above.

As will be readily apparent to one skilled in the art upon examination of the description above, instead of a movement of the wafer relative to the illuminating light beams, according to the present invention provision can also be made for the wafer to be held in stationary fashion in the wafer receiving device, and for the respective illuminating light beams instead to be deflected between the individual image acquisitions in order to scan the entire surface of the wafer sequentially, for example with the aid of tilting mirrors, microelectromechanical mirrors or mirrors produced with microsystems technology, or comparable optical elements. A central processor unit, for example computer 14 shown in FIG. 6, can be provided in order to control the respective incident illumination devices, the respective image sensing devices, and the movement device for moving the wafer relative to the illuminating light beams.

According to the present invention, images acquired in a bright-field configuration and in a dark-field configuration are not mutually influenced. This is achieved, in accordance with the first embodiment of the present invention described above, by asynchronously timed exposure of bright-field and dark-field image regions, and in accordance with the second embodiment of the present invention described above, by separation by color. In this fashion both the advantages of detecting defects in a bright-field configuration and the advantages of detecting defects in a dark-field configuration can be achieved in a single wafer inspection apparatus, along with high throughput for the wafer inspection apparatus.

As will be readily apparent to one skilled in the art upon examination of the description above, a further aspect of the present invention is directed toward a corresponding method for detecting defects and/or particles on a surface of a wafer, that method preferably being controlled in the manner described above with the aid of a control program stored on a computer-readable medium.

The invention claimed is:

1. A method for optically inspecting a surface of a wafer comprising the steps of:
    illuminating a region on the surface of the wafer with at least one first incident illuminating light beam for a bright-field illumination, the at least one first incident illuminating light beam being provided by a first incident illumination device in a bright-field configuration;
    illuminating another region on the surface of the wafer with at least one second incident illuminating light beam for a dark-field illumination, the at least one second incident illuminating light beam being provided by a second incident illumination device in a dark -field configuration;
    sequentially scanning the at least one first and the at least one second incident illuminating light beams over the surface of the wafer with a relative movement of the wafer with respect to the first and the second incident illuminating light beams; and
    acquiring a plurality of images of illuminated regions in a bright-field configuration and acquiring a plurality of images of the illuminated regions in a dark-field configuration;
    wherein the images of the illuminated regions in the dark-field configuration have a spatial offset from the images of the illuminated regions in the bright-field configuration; and
    wherein the relative movement of the wafer with respect to the at least one first and the at least one second incident illuminating light beams is performed by at least one of the group consisting of: deflecting at least one of the at least one first and at least one second incident illuminating light beams, and moving the wafer,
    wherein illuminating the regions on the surface of the wafer with the at least one first and at least one second incident illuminating light beams is performed asynchronously or simultaneously.

2. The method as defined in claim 1, wherein the sequential scanning the surface of the wafer is performed in a continuous or timed fashion.

3. The method as defined in claim 1, wherein acquiring the images in the bright-field configuration and the images in the dark-field configuration is performed alternatively.

4. The method as defined in claim 1, wherein in the step of acquiring a plurality of images, at least two images are acquired in the dark-field configuration between acquiring two images in the bright-field configuration.

5. The method as defined in claim 4, wherein acquiring the at least two images in the dark-field configuration is performed in a time-offset fashion.

6. The method as defined in claim 1, wherein the images in the bright-field configuration are acquired such that they correspond to regions on the surface of the wafer that are arranged with a periodic offset from one another.

7. The method as defined in claim 6, wherein the images acquired in the dark-field configuration are acquired at a predetermined offset relative to the regions that correspond to the images in the bright-field configuration.

8. The method as defined in claim 1, wherein the images acquired in the bright-field configuration correspond to a sub-region of a die.

9. The method as defined in claim 1, wherein images are acquired simultaneously in the dark-field configuration and in the bright-field configuration.

10. The method as defined in claim 9, wherein the at least one first and the at least one second incident illuminating light beams are polychromatic, and wherein images of illuminated regions in the bright-field configuration and in the dark-field configuration are acquired in corresponding different colors.

11. The method as defined in claim 9, wherein the at least one first and the at least one second incident illuminating light beams are monochromatic of one predefined color, and wherein images being acquired in the bright-field configuration have a lower incident illuminating light beam intensity than the images being acquired in the dark-field configuration.

12. The method as defined in claim 10, wherein images of illuminated regions are acquired in one predefined color in the bright-field configuration, and wherein images of illuminated regions are acquired in multiple predefined colors in the dark-field configuration.

13. The method as defined in claim 10, wherein images of illuminated regions are acquired in one predefined color in the dark-field configuration, and wherein images of illuminated regions are acquired in multiple predefined colors in the bright-field configuration.

14. The method as defined in claim 10, wherein images of illuminated regions are acquired in a blue color in the dark-field configuration, and are acquired in a red color and a green color in the bright-field configuration.

15. The method as defined in claim 1, further comprising arranging the wafer in a definable orientation on a wafer receiving device.

16. The method as defined in claim 15, wherein the at least one first and the at least one second incident illuminating light beams define respective illumination axes of each beam, so that a projection of the respective illumination axes onto the surface of the wafer with the features on the surface forms a predefined angle of 45 degrees or 90 degrees.

17. The method as defined in claim 16, wherein for an image acquired in the dark-field configuration, the projection of the respective illumination axes of the respective incident illuminating light beams onto the surface of the wafer forms an angle of approximately 45 degrees; and wherein for another image acquired in the dark-field configuration, the projection of the respective illumination axes of the respective incident illuminating light beams onto the surface of the wafer forms an angle of approximately 90 degrees.

* * * * *